(12) United States Patent
Andersson

(10) Patent No.: US 9,005,202 B2
(45) Date of Patent: Apr. 14, 2015

(54) IMPLANT ABUTMENT

(75) Inventor: Marcus Andersson, Göteborg (SE)

(73) Assignee: Cochlear Limited, Macquarie University, NSW (AU)

( * ) Notice: Subject to any disclaimer, the term of this patent is extended or adjusted under 35 U.S.C. 154(b) by 945 days.

(21) Appl. No.: 12/601,801

(22) PCT Filed: May 20, 2008

(86) PCT No.: PCT/SE2008/000337
§ 371 (c)(1),
(2), (4) Date: May 21, 2010

(87) PCT Pub. No.: WO2008/143574
PCT Pub. Date: Nov. 27, 2008

(65) Prior Publication Data
US 2010/0249784 A1 Sep. 30, 2010

(30) Foreign Application Priority Data
May 24, 2007 (SE) ........................................ 0701244

(51) Int. Cl.
*A61B 17/58* (2006.01)
*H04R 25/00* (2006.01)
*A61F 2/00* (2006.01)

(52) U.S. Cl.
CPC ............ *H04R 25/606* (2013.01); *A61F 2/0077* (2013.01); *H04R 2460/13* (2013.01)

(58) Field of Classification Search
USPC ............... 606/76, 77, 300, 305, 308; 381/326
See application file for complete search history.

(56) References Cited

U.S. PATENT DOCUMENTS

| | | | |
|---|---|---|---|
| 4,052,754 A | | 10/1977 | Homsy |
| 4,498,461 A | | 2/1985 | Hakansson |
| 4,612,915 A | * | 9/1986 | Hough et al. .................... 600/25 |
| 4,645,504 A | * | 2/1987 | Byers .............................. 623/10 |
| 4,818,559 A | * | 4/1989 | Hama et al. ................... 427/2.27 |
| 4,915,628 A | * | 4/1990 | Linkow et al. ................ 433/173 |
| 5,026,397 A | | 6/1991 | Aoki et al. |
| 5,049,074 A | * | 9/1991 | Otani et al. .................... 433/173 |
| 5,456,717 A | * | 10/1995 | Zweymuller et al. ....... 623/23.17 |
| 5,645,580 A | * | 7/1997 | Moaddeb et al. ............. 607/122 |
| 5,735,790 A | * | 4/1998 | Håkansson et al. ............. 600/25 |
| 5,857,958 A | * | 1/1999 | Ball et al. ......................... 600/25 |
| 5,951,601 A | * | 9/1999 | Lesinski et al. ................ 623/10 |
| 6,589,216 B1 | * | 7/2003 | Abbott et al. ................. 604/279 |

(Continued)

FOREIGN PATENT DOCUMENTS

| CA | 1068052 A1 | 12/1979 |
|---|---|---|
| EP | 0367354 | 5/1990 |

(Continued)

OTHER PUBLICATIONS

International Search Report. PCT/SE2008/000337. Mailed Jul. 16, 2008.

*Primary Examiner* — Christian Sevilla
(74) *Attorney, Agent, or Firm* — Lowe Hauptman & Ham, LLP

(57) ABSTRACT

The present invention relates to a percutaneous implant abutment for bone anchored implant devices adapted to be anchored in the craniofacial region of a person, such as bone anchored hearing aids. The abutment comprises a skin penetration body having a skin contacting surface. The skin contacting surface has been modified.

19 Claims, 2 Drawing Sheets

(56) References Cited

U.S. PATENT DOCUMENTS

| | | |
|---|---|---|
| 6,705,985 B2 * | 3/2004 | Easter et al. .................... 600/25 |
| 7,806,693 B2 * | 10/2010 | Hurson ......................... 433/174 |
| 8,469,908 B2 * | 6/2013 | Asfora ........................... 601/46 |
| 2001/0047175 A1 * | 11/2001 | Doubler et al. ................. 606/73 |
| 2003/0176866 A1 * | 9/2003 | Westerkull ..................... 606/73 |
| 2004/0132143 A1 * | 7/2004 | DeAngelis et al. ............. 435/89 |
| 2004/0204686 A1 | 10/2004 | Porter et al. |
| 2004/0215164 A1 * | 10/2004 | Abbott et al. ................. 604/514 |
| 2005/0026113 A1 * | 2/2005 | Chen et al. .................... 433/173 |
| 2005/0106534 A1 * | 5/2005 | Gahlert ......................... 433/173 |
| 2005/0113834 A1 * | 5/2005 | Breitenstien et al. ........... 606/73 |
| 2005/0142163 A1 * | 6/2005 | Hunter et al. ................. 424/423 |
| 2006/0050913 A1 * | 3/2006 | Westerkull .................... 381/326 |
| 2006/0093175 A1 | 5/2006 | Westerkull |
| 2006/0241592 A1 * | 10/2006 | Myerson et al. ................ 606/61 |
| 2007/0009853 A1 * | 1/2007 | Pitulia .......................... 433/173 |
| 2007/0270631 A1 * | 11/2007 | Nelson et al. ................... 600/12 |
| 2009/0082817 A1 * | 3/2009 | Jinton et al. .................. 606/301 |

FOREIGN PATENT DOCUMENTS

| | | |
|---|---|---|
| JP | 61-92852 | 7/1994 |
| WO | WO 01/97718 | 12/2001 |
| WO | 2004091432 A2 | 10/2004 |
| WO | 2005037153 A1 | 4/2005 |

* cited by examiner

IMPLANT ABUTMENT

CROSS-REFERENCE TO RELATED APPLICATIONS

This application is a national stage application under 35 USC §371(c) of PCT Application No. PCT/SE2008/000337, entitled "IMPLANT ABUTMENT," filed on May 20, 2008, which claims priority from Swedish Patent Application No. 0701244-6, filed on May 24, 2007. This application is related to commonly owned and co-pending U.S. Utility patent application entitled "VIBRATOR FOR BONE CONDUCTING HEARING DEVICES," filed Nov. 24, 2009, which is a national stage application of PCT Application No. PCT/SE2008/000336, filed May 21, 2008. This application is also related to commonly owned and co-pending U.S. Utility patent application entitled "ANCHORING ELEMENT" which is a national stage application under 35 USC §371 (c) of PCT Application No. PCT/SE2008/000338, filed on May 21, 2008. The entire disclosure and contents of the above applications are hereby incorporated by reference herein.

BACKGROUND

1. Field of the Invention

The present invention relates generally to bone anchored implant devices, and more particularly, to a percutaneous implant abutment for bone anchored implant devices adapted to be anchored in the craniofacial region of a person.

2. Related Art

There are a variety of medical devices that include a bone anchored implant device. An example of such medical devices is the, bone conduction hearing aid devices such as bone anchored hearing implants. An example of a bone anchored hearing implant is the Baha®, commercially available from Cochlear Bone Anchored Solutions AB in Göteborg, Sweden. The Baha® and other bone anchored implant devices comprise an external unit which transforms sound to mechanical vibrations which are conducted via the abutment and the fixture into the bone of the skull. The vibrations are transmitted mechanically via the skull bone directly to the inner ear of a person with impaired hearing and allows for the hearing organ to register the sound. A hearing aid device of the BAHA® type is connected to an anchoring element in the form of an implanted titanium screw installed in the bone behind the external ear. Sound is transmitted via the skull bone to the cochlea irrespective of a disease in the middle ear. The bone anchoring principle means that the skin is penetrated which makes the vibratory transmission very efficient.

This type of hearing aid device has been a revolution for the rehabilitation of patients with certain types of impaired hearing, but also as anti-stuttering means. It is very convenient for the patient and almost invisible with normal hair styles. It can easily be connected to the implanted titanium fixture by means of a bayonet coupling or a snap in coupling. One example of this type of hearing aid device is described in U.S. Pat. No. 4,498,461 and in SE 9702164-6 it is described a one-piece implant of this type, in which the fixture is integrated with a first coupling device. In WO 2005/037153 it is described how this type of hearing aid device can be used as an anti-stutte-ring device.

A well known problem with percutaneous implants is the infections and inflammation at the skin-implant interface. The infections are a result of bacterial colonization occurring at the area around the interface. There is generally a lack of integration of the skin to the implant which results in a gap between the two. This gap is unfortunately an ideal environment for the bacteria and if this zone is not properly managed, it is likely that an infection will occur. By creating an integration of the skin to the implant the adverse skin reactions associated with bone anchored percutaneous implants are expected to be reduced.

Creating integration between the skin and the implant requires that the implant is suitable for this purpose and that the soft tissue does not dissociate itself from the skin penetrating implant abutment by encapsulating the abutment in fibrous tissue.

In the field of dental implants it is previously known to use different types of abutments which penetrate the oral mucosa. However, it should be understood that there is a physiological difference between breaching the skin barrier compared to the oral mucosa. In the oral cavity the skin is not involved and there is another type of force situation. In contrast to dental implants the present invention relates to extraoral implants.

It is recognized that bone anchored percutaneously implants are subjected to mostly shear forces, while percutaneously implants which are not bone anchored are subjected to several other types of forces, such as pull and torsion. Such different types of forces are also mostly involved in dental applications. Mostly shear forces are especially the case for implants with inherent movements such as bone anchored hearing implants due to the generation of vibratory movements.

It is also recognized that the effect that the shear forces has on the skin leads to tissue damage not only from a mechanical point of view but, more importantly, an indirect biological reaction which leads to foreign body reaction or dissociation from the material (encapsulation of the implant by fibrous tissue, etc). Some reactions are acute and some are noticed after several weeks.

SUMMARY

In one aspect of the present invention, a percutaneous implant for bone anchored implant devices adapted to be anchored in the craniofacial region of a person is provided. The implant comprises: a screw-shaped bone anchoring element; an abutment, comprising: a skin penetration body having a skin contacting surface; and a biocompatible coating disposed on the skin contacting surface.

BRIEF DESCRIPTION OF THE DRAWINGS

Illustrative embodiments of the present invention will be described herein with reference to the accompanying figures, in which.

DETAILED DESCRIPTION

The present invention relates generally to bone anchored implant devices, and more particularly, to a percutaneous implant abutment for bone anchored implant devices adapted to be anchored in the craniofacial region of a person, such as bone anchored hearing aids. Implant devices of this type normally comprise a screw-shaped bone anchoring element (fixture) for permanent anchorage in the bone tissue and an abutment sleeve for skin penetration. The complete structure can either be in one piece or the skin penetrating abutment could be connected to the fixture prior, during or after the implantation procedure by means of a screw connection or the like.

Figure 1:
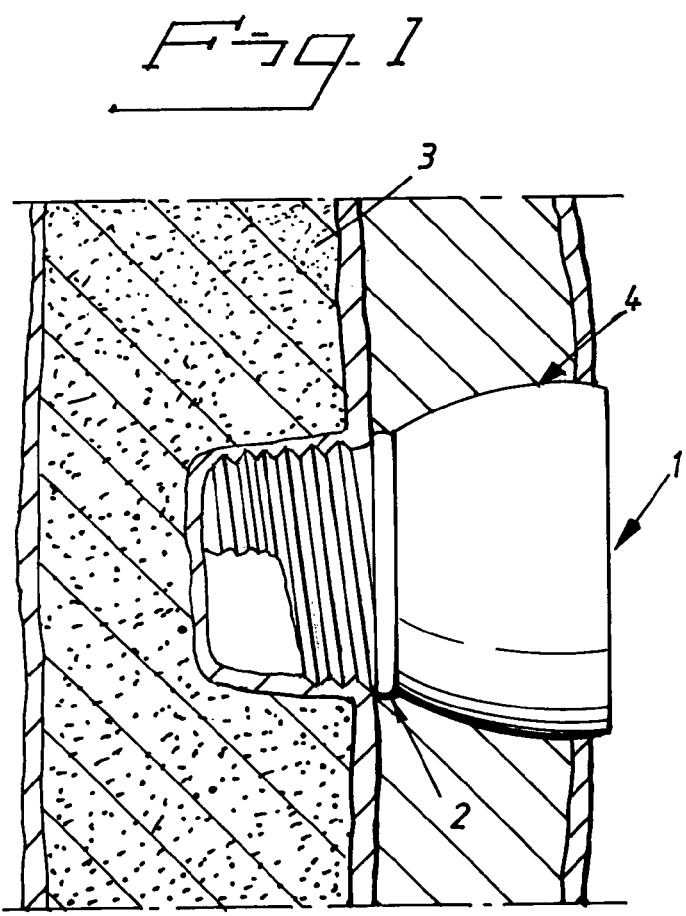
FIG. 1 illustrates an implant according to one embodiment of the present invention anchored in the bone in the craniofacial region of a person.

FIG. 1 illustrates a percutaneous implant 1 in accordance with embodiments of the present invention anchored in the bone in the cranio facial region of a person. The implant is may be used for a bone anchored hearing aid or the like. The implant comprises a screw-shaped bone anchoring element (fixture) 2 for permanent anchorage in the bone tissue 3 and an abutment device 4 for skin 5 penetration. The complete structure can either be in one piece or the skin penetrating abutment 4 could be connected to the fixture prior, during or after the implantation procedure by means of a screw connection or the like. The screw-shaped anchoring element, the so-called fixture 2 is made of titanium which has a known ability to integrate with the surrounding bone tissue, so-called osseointegration. The fixture has a threaded part 2a which is intended to be installed into the skull bone and a flange 2b which functions as a stop when the fixture is installed into the skull bone. The apical part of the fixture has a known tapping ability with in this case three self-tapping edges 2c. A fixture of this type is described in the above-mentioned SE 0002627-8 and will therefore not be described in any detail here.

The skin penetrating part, the abutment 4 of the implant, comprises a substantially conical abutment sleeve. Conical abutment sleeves are previously known per se as separate components or as an integral part with the fixture, a one-piece implant. The abutment sleeve is provided with a first coupling part in order to cooperate with a second coupling part (not shown) by means of snap-in action or the like.

According to embodiments of the present invention the shear modulus of the skin contacting part of the percutaneous implant abutment 4 has been reduced. Preferably the shear modulus should be less than approximately 35 GPa.

Figure 2:
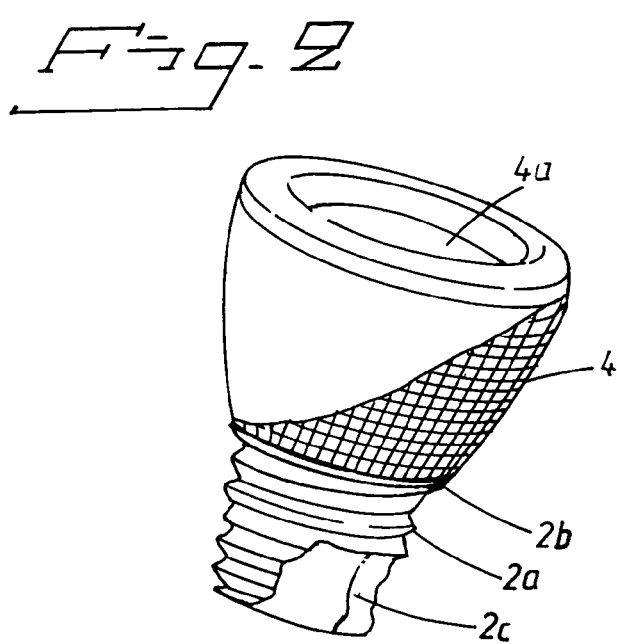
FIG. 2 illustrates an implant according to embodiments of the present invention for bone anchorage.

Specifically, the shear modulus is reduced by a modification of the surface of the skin contacting part of the percutaneous implant abutment, illustrated by the structured abutment surface in FIG. 2. According to a preferred embodiment the surface of the skin contacting part of the percutaneous implant abutment is coated with a biocompatible polymer or a ceramic material with a thickness of approximately 0.001 µm to approximately-50 µm. The coating is applied in such a way that non-interconnected pores or crevices are created. Generally the coating should be applied in such a way that a structured surface such as a porous surface or a surface with indentations or a fibrous surface is obtained. A typical porous surface is illustrated by the SEM picture in FIG. 4.

The polymer coating is comparatively soft and decreases the shear stresses on the skin. In certain embodiments, a layer of a porous polymer is used for the coating with a thickness of about 30 nm. Such design is allowing the skin to heal into the polymer matrix.

Also a polymer containing a pharmaceutical drug that increases the production of extra-cellular matrix proteins in the soft tissue, such as collagen or keratin, might be used. The increased stability of the tissue increases the resistance to shear stress.

Also other types of materials might be used for increasing the skin tissue integration. Specifically, chemical substances such as pharmaceutical drugs and antioxidants, or biochemical substances such as proteins, biopolymers, growth factors, DNA, RNA or biominerals might be used. These substances are then associated to the implant with a purpose of increasing the amount of, or number of connections to extra cellular matrix proteins. Antibiotic, steroid or anti-inflammatory substances might also be used.

As an alternative to said coatings or substances, or in combination, a surface enlargement treatment can be provided to the surface of the skin contacting part of the percutaneous implant in order to increase the surface roughness. Such treatment can be achieved by using techniques that includes grit-blasting, polishing, micro-machining, laser treatment, turning, anodic oxidation, oxidation, chemical etching, sintering or plasma deposition of a titanium surface. Preferably such treatment should result in a 10% surface increase, compared to a conventional machined surface and a roughness value Sa of approximately 0.5 µm to approximately-10 µm, measured by means of White Light Interferometry.

Figure 3:
FIG. 3 is a LM picture of the interface between the skin and the contacting part of the implant abutment.

FIG. 3 is a LM picture of the interface between the skin 5 and the contacting part of the implant abutment 4 of a polyurethane coated titanium material. The figure illustrates the situation after a healing period of 8 days and indicates a substantial integration of the abutment into the skin 5.

Figure 4:
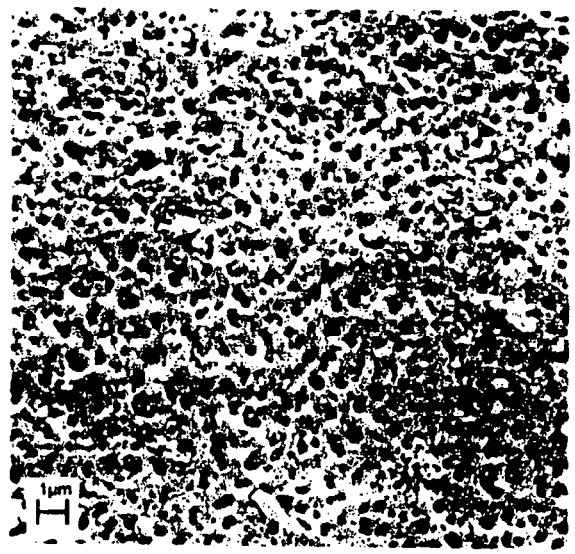
FIG. 4 is a SEM picture of the surface structure of the skin contacting part of the implant abutment.

FIG. 4 is a SEM picture of the surface structure of the skin contacting part of the implant abutment having an anodically oxidized surface.

It should be understood that only that part of the abutment surface which is in contact with the skin need to be modified. Other parts of the abutment such as the lower and upper end surfaces, i.e. the surfaces connected to the fixture and the coupling device respectively, might have a conventional, machined and/or polished surface.

According to one embodiment of the present invention, the surface of the skin contacting part of the percutaneously implant abutment is coated with a biocompatible polymer with a thickness of approximately 0.001 µm-to approximately 50 µm. According to a another embodiment, the surface of the skin contacting part of the percutaneously implant abutment is coated with a ceramic material with a thickness of 0.001 µm-to approximately 50 µm.

According to another embodiment, a surface enlargement treatment has been provided to the surface of the skin contacting part of the percutaneously implant abutment. Preferably a 10% surface increase, compared to a conventional machined surface, is created resulting in a roughness value Sa of 0.5 µm-to approximately 10 µm.

It should be understood that there are percutaneous implant as such that are made of polymers (catheters etc) but they are not bone anchored and they are not exposed to the typical shear forces that are the case for implants with inherent movements such as bone anchored hearing implants due to the generation of vibratory movements.

An advantage of embodiments of the present invention is to provide an implant abutment in which the shear forces between the implant abutment and the skin have been reduced. This improves wound healing and integration around bone anchored percutaneous implants.

According to another feature of embodiments of the present invention, the shear modulus of the skin contacting part of the percutaneously implant abutment is reduced. Preferably the shear modulus should be less than approximately 35 GPa.

In certain embodiments, the implant design includes a flange or a skirt perpendicular to the abutment orientation in order to mechanically increase the surface area and stability and thereby also reduce the shear stress on the implant-skin interface. Also the implant design might include one or more retention grooves or waists. Otherwise, however, the abutment should be designed without any sharp edges or corners in order to simplify the surface modification procedure.

Further features and advantages of the present invention are described in commonly owned and co-pending U.S. Utility patent application entitled "VIBRATOR FOR BONE CONDUCTING HEARING DEVICES," filed Nov. 24, 2009, which is a national stage application of PCT Application No. PCT/SE2008/000336, filed May 21, 2008; and commonly owned and co-pending U.S. Utility patent application entitled "ANCHORING ELEMENT" which is a national stage application under 35 USC §371 (c) of PCT Application No. PCT/SE2008/000338, filed on May 21, 2008. The content of these applications are hereby incorporated by reference herein.

It will be appreciated by persons skilled in the art that numerous variations and/or modifications may be made to the invention as shown in the specific embodiments without departing from the spirit or scope of the invention as broadly described. Specifically it should be understood that any combinations of the said surface modifications could be used, e.g. using composites, structured ceramic coatings, polymer/pharmaceutical drug coatings, anodized flange etc. The present embodiments are, therefore, to be considered in all respects as illustrative and not restrictive.

The invention claimed is:

1. A percutaneous implant for bone anchored implant devices adapted to be anchored in the craniofacial region of a person, comprising:
    a bone anchoring element comprising a threaded exterior surface; and
    an abutment, comprising:
        a skin penetration body having a skin contacting surface; and
        a biocompatible coating disposed on the skin contacting surface, wherein the biocompatible coating has a composition and thickness such that the coated skin contacting surface has a shear modulus that is less than approximately 35 GPa.

2. The implant according to claim 1, wherein the biocompatible coating comprises a biocompatible polymer having a thickness of approximately 0.001 μm to approximately 50 μm.

3. The implant according to claim 1, wherein the biocompatible coating comprises a ceramic material having a thickness of approximately 0.001 μm to approximately 50 μm.

4. The implant according to claim 1, wherein the biocompatible coating has a roughness value (Sa) of approximately 0.5 μm-10 μm.

5. The implant according to claim 2, wherein the polymer coating comprises:
    a porous coating on the skin contacting surface.

6. The implant according to claim 2, wherein the polymer coating comprises:
    a coating having non-interconnected pores or crevices.

7. The implant according to claim 2, wherein the polymer coating comprises:
    a coating that is porous and has a thickness of approximately 30 nm.

8. The implant according to claim 2, wherein the polymer coating comprises:
    a coating containing a pharmaceutical drug that increases the production of extra-cellular matrix proteins in the soft tissue, such as collagen or keratin.

9. The implant according to claim 2, wherein the polymer coating comprises:
    a coating including one or more chemical substances selected from the group comprising:
    pharmaceutical drugs, antioxidants, or biochemical substances configured to increase at least one of the amount and number of connections to extra cellular matrix proteins.

10. The implant according to claim 2, wherein the polymer coating comprises:
    a coating including antibiotic, steroid or anti-inflammatory substances.

11. The implant according to claim 1, wherein only a part of the abutment which is in contact with the skin is coated.

12. The implant according to claim 1, further comprising:
    a flange perpendicular to the skin penetration body in order to mechanically increase the surface area and stability, thereby reducing the shear stress on the implant-skin interface.

13. The implant according to claim 1, further comprising:
    one or more retention grooves.

14. The implant according to claim 1, further comprising:
    a sleeve-shaped body having a rounded outer surface without any sharp edges.

15. The implant according to claim 5, wherein the porous surface comprises a plurality of indentations.

16. The implant according to claim 5, wherein the porous surface comprises a fibrous surface.

17. The implant according to claim 9, wherein the biochemical substances are selected from the group comprising: proteins, biopolymers, growth factors, DNA, RNA or biominerals.

18. A percutaneous implant for bone anchored implant devices adapted to be anchored in the craniofacial region of a person, comprising:
    a bone anchoring element comprising a threaded exterior surface: and
    an abutment, comprising:
        a skin penetration body having a skin contacting surface; and
        a biocompatible coating disposed on the skin contacting surface, wherein the biocompatible coating comprises a biocompatible polymer having a thickness of approximately 0.00 1 μm to approximately 50 μm.

19. A percutaneous implant for bone anchored implant devices adapted to be anchored in the craniofacial region of a person, comprising:
    a bone anchoring element comprising a threaded exterior surface; and
    an abutment, comprising:
    a skin penetration body having a skin contacting surface; and
    a biocompatible coating disposed on the skin contacting surface, wherein the biocompatible coating comprises a ceramic material having a thickness of approximately 0.001 μm to approximately 50 μm.

* * * * *